United States Patent
Coumans

(10) Patent No.: US 11,696,958 B2
(45) Date of Patent: Jul. 11, 2023

(54) DUAL CONJUGATION PROCESS FOR PREPARING ANTIBODY-DRUG CONJUGATES

(71) Applicant: Byondis B.V., Nijmegen (NL)

(72) Inventor: Rudy Gerardus Elisabeth Coumans, Nijmegen (NL)

(73) Assignee: Byondis B.V., Nijmegen (NL)

( * ) Notice: Subject to any disclaimer, the term of this patent is extended or adjusted under 35 U.S.C. 154(b) by 735 days.

(21) Appl. No.: 16/616,045

(22) PCT Filed: May 22, 2018

(86) PCT No.: PCT/EP2018/063328
§ 371 (c)(1),
(2) Date: Nov. 22, 2019

(87) PCT Pub. No.: WO2018/215427
PCT Pub. Date: Nov. 29, 2018

(65) Prior Publication Data
US 2020/0276331 A1    Sep. 3, 2020

(30) Foreign Application Priority Data

May 23, 2017   (EP) ..................... 17172449
May 23, 2017   (EP) ..................... 17172450

(51) Int. Cl.
| | | |
|---|---|---|
| A61K 47/68 | (2017.01) | |
| A61K 31/66 | (2006.01) | |
| C07K 16/30 | (2006.01) | |
| A61K 39/00 | (2006.01) | |

(52) U.S. Cl.
CPC .......... *A61K 47/6873* (2017.08); *A61K 31/66* (2013.01); *C07K 16/30* (2013.01); *A61K 47/6803* (2017.08); *A61K 2039/505* (2013.01); *C07K 2317/567* (2013.01)

(58) Field of Classification Search
CPC .............. C07K 16/30; C07K 2317/567; A61K 47/6803; A61K 2039/505
See application file for complete search history.

(56) References Cited

U.S. PATENT DOCUMENTS

| | | | |
|---|---|---|---|
| 4,816,567 A | 3/1989 | Cabilly et al. | |
| 10,407,743 B2* | 9/2019 | Ariaans | A61P 35/00 |
| 10,814,009 B2* | 10/2020 | Coumans | A61K 47/6809 |
| 11,008,400 B2* | 5/2021 | Van der Lee | A61K 47/6851 |
| 11,104,968 B2* | 8/2021 | Ariaans | C07K 16/30 |
| 11,136,633 B2* | 10/2021 | Ariaans | A61P 35/00 |

FOREIGN PATENT DOCUMENTS

| | | | | |
|---|---|---|---|---|
| WO | 2011/133039 A2 | 10/2011 | | |
| WO | WO-2015057699 A2 * | 4/2015 | .......... | A61K 39/395 |
| WO | 2015/123265 A1 | 8/2015 | | |
| WO | 2015/177360 A1 | 11/2015 | | |
| WO | 2017/137628 A1 | 8/2017 | | |

OTHER PUBLICATIONS

Sutherland et al., "SGN-CD33A: a novel CD33-targeting antibody-drug conjugate using a pyrrolobenzodiazepine dimer is active in models of drug-resistant AML," Blood, Aug. 22, 2013, vol. 122, No. 8, pp. 1455-1463.
Köhler et al., "Continuous cultures of fused cells secreting antibody of predefined specificity," Nature, Aug. 7, 1975, vol. 256, pp. 495-497.
Clackson et al., "Making antibody fragments using phage display libraries," Nature, Aug. 15, 1991, vol. 352, pp. 624-628.
Marks et al., "Human Antibodies from V-gene Libraries Displayed on Phage," J. Mol. Biol. 1991, 222, pp. 581-597.
Kabat, E.A. et al., Sequences of Proteins of Immunological Interest, 5th Ed. Public Health Service, National Institutes of Health, Bethesda, MD, NIH publication No. 91-3242, pp. 662, 680, 689 (1991).
M. Bornand et al., "Mechanistically Designed Dual-Site Catalysts for the Alternating ROMP of Norborene and Cyclooctene," Organometallics, 2007, vol. 26, No. 14, pp. 3585-3596.
T. Schultz et al., "Palladium (II) Complexes with Chelating P, O-Ligands as Catalysts for the Heck Reaction," Synthesis, 2005, No. 6, pp. 1005-1011.
R.E. Hansen et al., "An introduction to methods for analyzing thiols and disulfides: Reactions, reagents and practical considerations," Analytical Biochemistry, 2009, 394, 147-158.
Dokter et al., "Preclinical Profile of the HER2-Targeting ADC SYD983/SUD985: Introduction of a New Duocarmycin-Based Linker-Drug Platform," Mol. Cancer Ther., Nov. 2014, 13(11), pp. 2618-2629.
Kirley et al., "Selective disulfide reduction for labeling and enhancement of Fab antibody fragments," Biochemical and Biophysical Research Communications, Elsevier, Amsterdam, NL, vol. 480, No. 4, Oct. 29, 2016, pp. 752-757.
Elgersma et al., "Design, Synthesis, and Evaluation of Linker-Duocarmycin Payloads: Toward Selection of HER2-Targeting Antibody-Drug Conjugate SYD985," Molecular Pharmaceutics, vol. 12, No. 6, Jun. 1, 2015, pp. 1813-1835.

* cited by examiner

*Primary Examiner* — Hong Sang
(74) *Attorney, Agent, or Firm* — Buscher Patent PLLC

(57) ABSTRACT

The present invention relates to a process for preparing antibody-drug conjugates and to antibody-drug conjugates wherein therapeutic moieties are conjugated to one or more engineered cysteines as well as to one or more reduced interchain cysteines via a cleavable or non-cleavable linker.

18 Claims, 5 Drawing Sheets

Specification includes a Sequence Listing.

SEQUENCE LISTING

<160> NUMBER OF SEQ ID NOS: 4

<210> SEQ ID NO 1
<211> LENGTH: 121
<212> TYPE: PRT
<213> ORGANISM: Artificial Sequence
<220> FEATURE:
<223> OTHER INFORMATION: HCVR anti-5T4 antibody 41C

<400> SEQUENCE: 1

```
Glu Val Gln Leu Val Glu Ser Gly Gly Asp Leu Ala Gln Pro Gly Gly
1               5                   10                  15

Ser Leu Arg Leu Ser Cys Ala Val Ser Gly Ile Asp Leu Ser Ser Tyr
            20                  25                  30

Gly Met Gly Trp Val Arg Gln Ala Cys Gly Lys Gly Leu Glu Trp Val
        35                  40                  45

Ser Ile Ile Ser Arg Asn Ser Val Thr Tyr Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Thr Ser Leu Arg Ala Glu Asp Thr Ala Leu Tyr Phe Cys Ala
                85                  90                  95

Arg Arg Ala Thr Tyr Ser Gly Ala Leu Gly Tyr Phe Asp Ile Trp Gly
            100                 105                 110

Gln Gly Thr Leu Val Thr Val Ser Ser
        115                 120
```

<210> SEQ ID NO 2
<211> LENGTH: 110
<212> TYPE: PRT
<213> ORGANISM: Artificial Sequence
<220> FEATURE:
<223> OTHER INFORMATION: LCVR anti-5T4 antibody

<400> SEQUENCE: 2

```
Glu Ile Val Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Thr
            20                  25                  30

Leu Ala Trp Tyr Gln Gln Lys Pro Gly Lys Ala Pro Lys Leu Leu Ile
        35                  40                  45

Tyr Asp Ala Phe Asp Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Tyr Ser Gly Thr Asn
                85                  90                  95

Val Asp Asn Ala Phe Gly Gln Gly Thr Lys Leu Glu Ile Lys
            100                 105                 110
```

<210> SEQ ID NO 3
<211> LENGTH: 19
<212> TYPE: PRT
<213> ORGANISM: Artificial Sequence
<220> FEATURE:
<223> OTHER INFORMATION: HC rabbit leader sequence

<400> SEQUENCE: 3

```
Met Gly Trp Thr Leu Val Phe Leu Phe Leu Leu Ser Val Thr Ala Gly
1               5                   10                  15
```

```
Val His Ser

<210> SEQ ID NO 4
<211> LENGTH: 20
<212> TYPE: PRT
<213> ORGANISM: Artificial Sequence
<220> FEATURE:
<223> OTHER INFORMATION: LC rabbit leader sequence

<400> SEQUENCE: 4

Met Val Ser Ser Ala Gln Phe Leu Gly Leu Leu Leu Leu Cys Phe Gln
1               5                   10                  15

Gly Thr Arg Cys
            20
```

DUAL CONJUGATION PROCESS FOR PREPARING ANTIBODY-DRUG CONJUGATES

REFERENCE TO SEQUENCE LISTING SUBMITTED VIA EFS-WEB

This application includes an electronically submitted sequence listing in .txt format. The .txt file contains a sequence listing entitled "P1716US00_PB-081_ST25.txt" created on Feb. 4, 2022 and is 3,151 bytes in size. The sequence listing contained in this .txt file is part of the specification and is hereby incorporated by reference herein in its entirety.

FIELD OF THE INVENTION

The present invention relates to a new process for conjugating therapeutic moieties via a cleavable or non-cleavable linker to antibodies. Furthermore, it relates to new antibody-drug conjugates.

BACKGROUND OF THE PRESENT INVENTION

Antibody-drug conjugates (ADCs) are an emerging class of targeted therapeutics, in which the specificity of antibodies and the potency of cytotoxic molecules are combined.

Cysteine-engineered antibodies are increasingly used for conjugation of a therapeutic moiety (e.g. a drug, toxin, or a chelator for a radioactive isotope), a fluorescent label or a hydrophilic polymer. The introduction of a cysteine residue at a suitable position of the antibody allows control of the site of conjugation and the obtained site-specific conjugates are more homogeneous than the conjugates obtained via wild-type conjugation, i.e. conjugation via reduced interchain cysteines. Site-specifically conjugated ADCs have generally demonstrated at least equivalent in vivo potency, improved pharmacokinetics (PK), and an expanded therapeutic window compared to wild-type conjugates. The first site-specific ADC in clinical trials, SGN-CD33A (Seattle Genetics), comprises a cleavable dipeptide linker (i.e., valine-alanine) and a DNA-cross-linking pyrrolobenzodiazepine (PBD) dimer as the drug, which is linked to a cysteine at heavy chain position S239C in the Fc part of IgG1 mAb h2H12, having an average drug-to-antibody ratio (DAR) of 1.9 (Sutherland et al., Blood, 2013, 122(8), 1455-1463). This low drug loading might not be suitable for every linker drug or for every type of cancer. For less potent toxins or for cancer types with a lower expression of target antigen, a higher DAR may be necessary. However, this may only become apparent in an advanced stage of development, when substantial time, effort and resources have been invested in the development of an antibody with one engineered cysteine in the heavy or light chain. Furthermore, when it is apparent that an average DAR of 1.9 is insufficient, additional cysteines must be engineered into the antibody, which requires new antibody development, and therefore new cell line development, which is a lengthy process. Additionally, determining the position of the one or more additional cysteines is not a trivial matter, because e.g. not all positions enable conjugation or some positions might result in ADCs with unacceptably high percentages of high molecular weight aggregates (HMW).

Therefore, new and more flexible conjugation processes, which can be used to easily tune the DAR of the resulting ADCs, without the necessity of undertaking a full new antibody development are still desired, as well as ADCs having acceptable antigen binding properties, pharmacokinetics, in vivo efficacy, therapeutic index, and/or stability.

BRIEF DESCRIPTION OF THE PRESENT INVENTION

The present invention relates to a process for preparing antibody-drug conjugates and to antibody-drug conjugates wherein therapeutic moieties are conjugated to one or more engineered cysteines as well as to one or more reduced interchain cysteines via a cleavable or non-cleavable linker.

DETAILED DESCRIPTION OF THE PRESENT INVENTION

Figure 1:
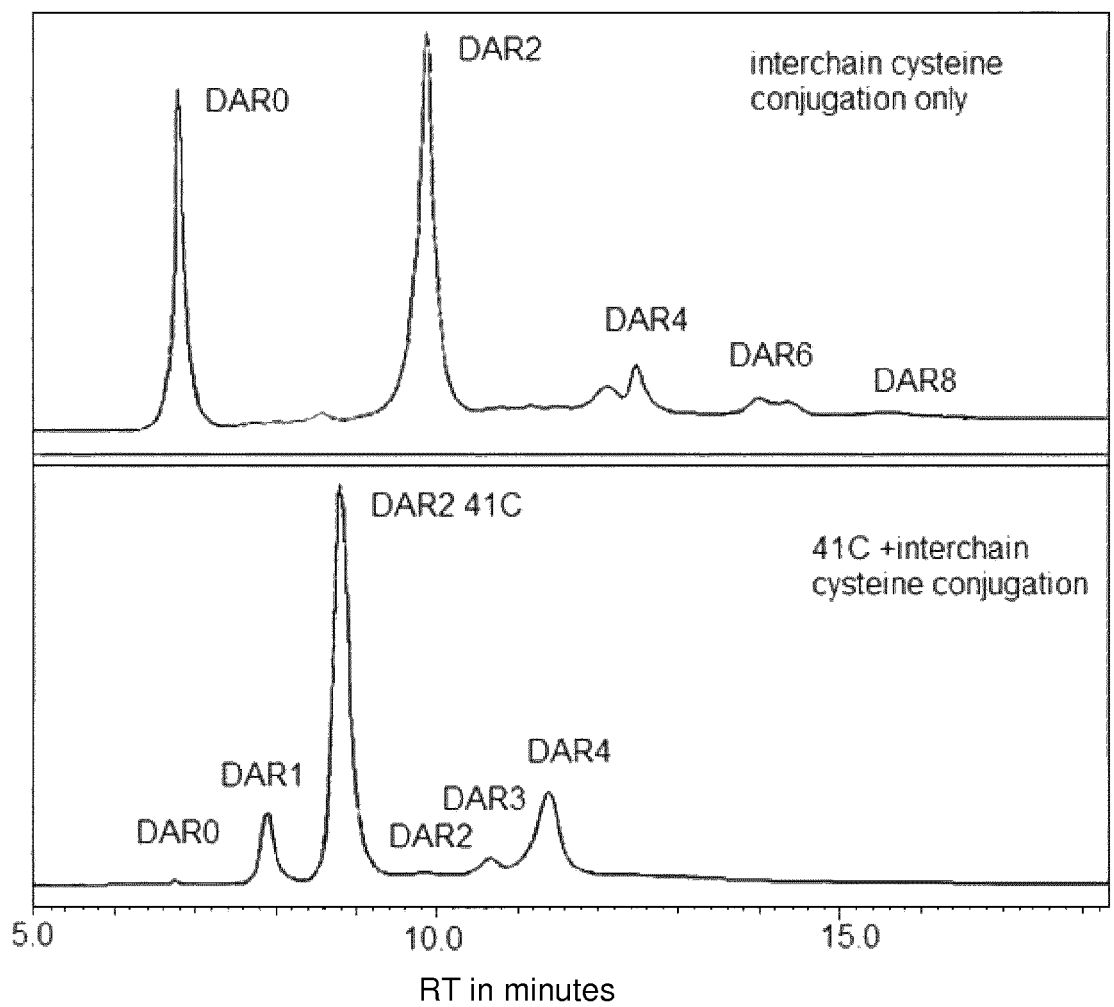
FIG. 1. HIC profile of the vc-seco-DUBA ADC 1d, conjugated via reduced interchain cysteines only, DAR 2.5 (upper panel) and of the vc-seco-DUBA ADC 1c, conjugated via both engineered cysteines at position HC41 and reduced interchain cysteines, DAR 2.6 (lower panel).

The present invention relates to a process for preparing antibody-drug conjugates and to antibody-drug conjugates wherein therapeutic moieties are conjugated to one or more engineered cysteines as well as to one or more reduced interchain cysteines via a cleavable or non-cleavable linker.

The term "antibody" as used throughout the present specification refers to a monoclonal antibody (mAb) comprising two heavy chains and two light chains or an antigen binding fragment thereof, wherein at least one interchain disulfide bond is present, e.g. a Fab, Fab' or F(ab)$_2$ fragment. Antibodies in accordance with the invention may be of any isotype such as IgG, IgA or IgM antibodies. Preferably, the antibody is an IgG antibody, more preferably an IgG1 or IgG2 antibody. The antibodies may be chimeric, humanized or human. Preferably, the antibodies are humanized. Even more preferably, the antibody is a humanized or human IgG antibody, most preferably a humanized or human IgG1 mAb. The antibody may have κ (kappa) or λ (lambda) light chains, preferably κ (kappa) light chains, i.e., a humanized or human IgG1-κ antibody.

In humanized antibodies, the antigen-binding complementarity determining regions (CDRs) in the variable regions of the HC and LC are derived from antibodies from a non-human species, commonly mouse, rat or rabbit. These non-human CDRs may be placed within a human framework (FR1, FR2, FR3 and FR4) of the variable regions of the HC and LC. Selected amino acids in the human FRs may be exchanged for the corresponding original non-human species amino acids to improve binding affinity, while retaining low immunogenicity. Alternatively, selected amino acids of the original non-human species FRs are exchanged for their corresponding human amino acids to reduce immunogenicity, while retaining the antibody's binding affinity. The thus humanized variable regions are combined with human constant regions.

The terms "monoclonal antibody" and "mAb" as used herein refer to an antibody obtained from a population of substantially homogeneous antibodies, i.e., the individual antibodies comprising the population are identical except for possible naturally-occurring mutations that may be present in minor amounts. Antibodies may be generated by immunizing animals with a mixture of peptides representing the desired antigen. B-lymphocytes are isolated and fused with myeloma cells or single B lymphocytes were cultivated for several days in the presence of conditioned medium and feeder cells. The myeloma or B lymphocyte supernatants containing the produced antibodies are tested to select suitable B lymphocytes or hybridomas. Monoclonal antibodies may be prepared from suitable hybridomas by the hybridoma methodology first described by Kohler et al., Nature, 1975, 256, 495-497. Alternatively, the RNA of suitable B-cells or lymphoma may be lysed, RNA may be isolated, reverse transcribed and sequenced. Antibodies may be made recombinant DNA methods in bacterial, eukaryotic animal or plant cells (see, e.g., U.S. Pat. No. 4,816,567). The "monoclonal antibodies" may also be isolated from phage antibody libraries using the techniques described in the art, e.g. in Clackson et al., Nature 199, 1352, 624-628 and Marks et al., J. Mol. Biol. 1991, 222, 581-597.

The term "cysteine engineered antibody" as used throughout the present specification refers to an antibody wherein one or more cysteine residues have been introduced by genetic engineering techniques, either by replacing one or more amino acid residues of the antibody with a cysteine, or by insertion of one or more cysteines into the primary amino acid sequence.

The term "antibody-drug conjugate (ADC)" as used throughout the present specification refers to an antibody as defined hereinabove, to which one or more therapeutic moieties are conjugated via a linker (linker drugs). The number of linker drugs conjugated to the antibody is usually referred to as drug-to-antibody ratio (DAR). Conjugation processes typically yield a heterogeneous mixture of different ADC molecules, i.e. different DAR species having different drug-to-antibody ratios. Therefore, the term "ADC" also refers to such mixtures of DAR species. The term "average DAR" refers to the average DAR of the population of such DAR species. As is well-known in the art, the DAR and drug load distribution can be determined, for example, by using hydrophobic interaction chromatography (HIC) or reversed phase high-performance liquid chromatography (RP-HPLC). HIC is particularly suitable for determining the average DAR.

The present invention relates to a process for preparing an antibody-drug conjugate comprising the steps of:
a. selectively reducing a cysteine-engineered antibody comprising reacting an antibody comprising one or more engineered cysteines at positions selected from heavy chain 40, 41, and 89 according to the Kabat numbering system, heavy chain 152, 153, 155, and 171 according to the Eu numbering system, light chain 40 and 41 according to the Kabat numbering system, and light chain 165 and 168 according to the Eu numbering system, with a compound according to formula (I), (II), (III), (IV), (V), (VI) or (VII)

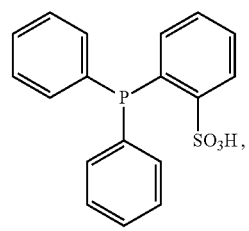

(I)

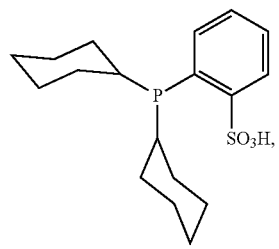

(II)

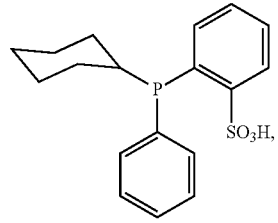

(III)

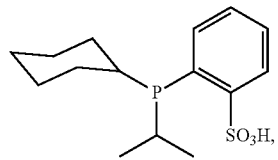

(IV)

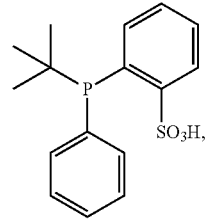

(V)

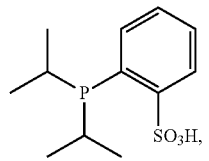

(VI)

-continued

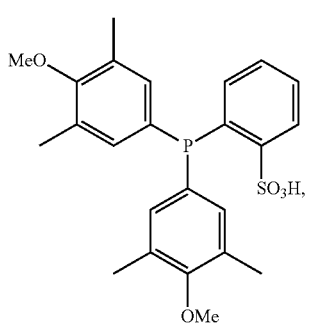

(VII)

or a salt thereof;
b. further reducing the selectively reduced antibody of step a. with an interchain disulfide bond reducing agent; and
c. conjugating therapeutic moieties to the further reduced antibody of step b. via cleavable or non-cleavable linkers.

In one embodiment of the present invention, the compound according to formula (I), (II), (III), (IV), (V), (VI) or (VII) is present in an amount of at least one molar equivalent per molar amount of engineered cysteine. This means that in order to selectively reduce an antibody having one engineered cysteine in the light chain or heavy chain, i.e. two engineered cysteines are present in the antibody, at least two moles of the compound are used per mole of antibody.

Preferred is a process wherein an amount of from 2 to 16 molar equivalents of the compound according to formula (I), (II), (III), (IV), (V), (VI) or (VII) per molar amount of engineered cysteine is used. If less than one molar equivalent per molar amount of engineered cysteine is used, complete reduction of all engineered cysteines is not achieved. The molar ratio of the compound per engineered cysteine affects the rate of reduction (uncapping) of the engineered cysteines, but it has no influence on the selectivity of the reduction.

Preferably, the invention relates to a process, wherein the antibody comprises one or more engineered cysteines at positions selected from heavy chain 40, 41, 152, and 153 and light chain 40, 41, and 165. More preferably, the antibody comprises one or more engineered cysteines at positions selected from heavy chain 41 and light chain 40 and 41. Most preferably, the antibody to be used in accordance with the process of the invention comprises an engineered cysteine at heavy chain 41, i.e. HC41C.

In the context of the present invention, Kabat numbering is used for indicating the amino acid positions of engineered cysteines in the heavy chain (HC) and light chain (LC) variable regions and Eu numbering is used for indicating the positions in the heavy chain and light chain constant regions of the antibody. The expression "Kabat numbering" refers to the numbering system used for heavy chain variable domains or light chain variable domains of the compilation of antibodies described in Kabat, E. A. et al., Sequences of Proteins of Immunological Interest, 5th Ed. Public Health Service, National Institutes of Health, Bethesda, Md. (1991).

The expression "Eu numbering" refers to the Eu index as in Kabat, E. A. et al., Sequences of Proteins of Immunological Interest, 5th Ed. Public Health Service, National Institutes of Health, Bethesda, Md., NIH publication no. 91-3242, pp. 662, 680, 689 (1991).

In accordance with the present invention, the cysteine-engineered antibody may be prepared by using conventional molecular cloning techniques or the heavy chain or light chain domain(s) of the antibody carrying the cysteine mutation(s) can be synthesized as such using known (peptide or DNA) synthesis equipment and procedures. Typically, procedures similar to those disclosed in WO2015/177360 are used.

The compound according to formula (I), (II), (III), (IV), (V), (VI) or (VII) reduces selectively the engineered cysteines of the antibody in the process of the invention. The compound according to formula (I) is 2-(diphenylphosphino)benzenesulfonic acid and the compound according to formula (II) is 2-(dicyclohexylphosphino)-benzenesulfonic acid. Phosphines (I) and (II) are commercially available as e.g. the sulfonic acid or the sodium sulfonate salt from various suppliers, e.g. Sigma-Aldrich. The compound according to formula (III), (IV), (V), (VI) or (VII) may be prepared by procedures known in the art (analogous to procedures disclosed in e.g., M. Bornand et al., Organometallics, 2007, 26(14), 3585-3596 and T. Schultz et al., Synthesis, 2005, 6, 1005-1011). The compounds according to formulae (I), (II), (III), (IV), (V), (VI) and (VII) are readily deprotonated in aqueous solution and may form corresponding sulfonate salts with cations present in the solution. Typical cations are, e.g., ammonium, tetramethylammonium, triethanolammonium, imidazolium, sodium, and potassium, i.e. cations present in commonly used buffer solutions for preparing ADCs.

Preferred in accordance with the present invention is a process wherein the cysteine-engineered antibody is reacted with a compound according to formula (I), (II), (III), (V), (VI) or (VII), or a salt thereof. More preferred in accordance with the present invention is a process wherein the cysteine-engineered antibody is reacted with a compound according to formula (I), (II) or (III), or a salt thereof. Even more preferred in accordance with the present invention is a process wherein the cysteine-engineered antibody is reacted with a compound according to formula (I) or (II), or a salt thereof. Most preferred in accordance with the present invention is a process wherein the cysteine-engineered antibody is reacted with a compound according to formula (I) or a salt thereof.

The present inventors found inter alia that by using a compound according to formula (I), (II), (III), (IV), (V), (VI) or (VII), the capped engineered cysteines at specific positions in the Fab cavity that is formed by the CH1, VH, VL and CL domains of the antibody are selectively reduced, while the interchain disulfide bonds formed by the native cysteine residues of the antibody, i.e. the interchain cysteines, are left intact.

The interchain disulfide bond reducing agent to be used in accordance with the process of the invention can be any agent suitable for reducing interchain cysteine disulfide bonds. Suitable interchain disulfide bond reducing agents are well known to the skilled person, see e.g. R. E. Hansen et al., Analytical Biochemistry, 2009, 394, 147-158. Typically, they are water soluble and have a negative redox potential at pH 7. The reducing agent may be a thiol or a phosphine. Suitable thiols include 1,4-(dithiobutyl)-2-amine (DTBA), glutathione, cysteine, 2-mercaptoethanol, 2-mercaptoethylamine, dithioerythritol (DTE), or dithiothreitol (DTT). Suitable phosphines include tris(3-sulfophenyl)phosphine, tris(2-carboxyethyl)phosphine (TCEP), tris(3-hydroxypropyl)phosphine (THPP), or tris(hydroxymethyl)phosphine. Preferred reducing agents are tris(3-sulfophenyl)phosphine, TCEP and DTT. The most preferred interchain disulfide bond reducing agent is TCEP.

The interchain disulfide bond reducing agent to be used in the process according to the invention is preferably present in an amount of more than 0.1 molar equivalents per molar equivalent of antibody. More preferably, the interchain disulfide bond reducing agent is present in an amount of at least 0.25 molar equivalents per molar equivalent of antibody. Even more preferably, the interchain disulfide bond reducing agent is present in an amount of from 0.25 to 3 or of from 0.25 to 2 molar equivalents per molar equivalent of antibody. Even more preferably, the interchain disulfide bond reducing agent is present in an amount of from 0.5 to 2 molar equivalents per molar equivalent of antibody, most preferably 0.5 to 1 molar equivalent per molar equivalent of antibody.

The process of the present invention is performed under mild conditions, i.e. conditions under which the antibody is stable. Typically, the process in accordance with the present invention is performed in a buffered aqueous solution. The cysteine-engineered antibodies that are produced in (mammalian) host cells and that are isolated and purified using conventional equipment and procedures may need a buffer exchange in order to obtain the optimal conditions for the selective reduction process in accordance with the present invention. Suitable buffered solutions include phosphate-buffered saline (PBS), citrate, histidine, acetate and succinate buffered aqueous solutions. Additional salts and other solutes (e.g. sucrose, trehalose, EDTA) may be present in the buffered aqueous solution. For the selective reduction step the buffered solutions preferably are acetate, histidine, or mixtures of acetate and histidine buffered solutions.

The reaction temperature is typically in the range of from 0° C. to 40° C., the pH is typically in the range of from 4 to 8.

For the selective reduction step a., a pH in the range of from 4 to 7 is preferred. More preferred for the selective reduction step is a pH in the range of from 5 to 6.

Typically, unreacted/excess compound of formula (I), (II), (III), (IV), (V), (VI) or (VII) is removed before further reducing the selectively reduced antibody, typically by ultrafiltration/diafiltration (UF/DF), tangential flow filtration (TFF) or active carbon filtration.

The above-described reaction conditions for the selective reduction step a. mainly affect the rate and degree of completion of the selective reduction process and/or the stability of the antibody.

The interchain disulfide bond reduction step b. and subsequent conjugation step c. in accordance with the present invention may be performed in a buffered aqueous solution, e.g. a citrate, a histidine or a succinate buffered aqueous solution, at a pH and temperature at which the antibody, the therapeutic moieties to be conjugated via cleavable or non-cleavable linkers (linker drugs), and the resulting antibody conjugate are stable. Typically, the pH is in the range of from 5 to 8, and the temperature is in the range of from 0° C. to 40° C.

For the interchain disulfide bond reduction and subsequent conjugation step, a pH in the range of from 6 to 8 is preferred, more preferred is a pH in the range of from 6.5 to 7.5, a pH in the range of from 6.8 to 7.3 is most preferred. A preferred buffered aqueous solution in which the interchain disulfide bond reduction step and subsequent conjugation step in accordance with the present invention are performed, comprises histidine.

Additional salts and other solutes (e.g. sucrose, trehalose, EDTA) may be present in the buffered aqueous solution. In case the moiety to be conjugated to the antibody is poorly water soluble, e.g. in case of a hydrophobic linker drug, the moiety may be dissolved in an organic, water-miscible solvent. Suitable solvents include dimethyl sulfoxide (DMSO), dimethyl acetamide (DMA), propylene glycol, and ethylene glycol.

The resulting ADCs may be purified using standard methods known to the person skilled in the art, e.g. active carbon filtration to remove excess linker drug and hydrophobic interaction chromatography (HIC) to remove any unreacted antibody.

The ADCs prepared according to the process of the present invention may be analyzed using analytical methods known in the art, e.g. high-performance liquid chromatography (HPLC), shielded hydrophobic phase HPLC (SHPC), hydrophobic interaction chromatography (HIC), and size-exclusion chromatography (SEC).

Typically, the antibody to be used in accordance with the invention is a monospecific or bispecific antibody or antibody fragment comprising at least one heavy chain and light chain variable region binding to a target selected from the group consisting of annexin A1, B7H4, CA6, CA9, CA15-3, CA19-9, CA27-29, CA125, CA242, CCR2, CCR5, CD2, CD19, CD20, CD22, CD30, CD33, CD37, CD38, CD40, CD44, CD47, CD56, CD70, CD74, CD79, CD115, CD123, CD138, CD203c, CD303, CD333, CEA, CEACAM, CLCA-1, CLL-1, c-MET, Cripto, DLL3, EGFL, EGFR, EPCAM, EPh (e.g. EphA2 or EPhB3), endothelin B receptor (ETBR), FAP, FcRL5 (CD307), FGFR (e.g. FGFR3), FOLR1, GCC, GPNMB, HER2, HMW-MAA, integrin α (e.g. αvβ3 and αvβ5), IGF1R, TM4SF1 (or L6 antigen), Lewis A like carbohydrate, Lewis X, Lewis Y, LIV1, mesothelin, MUC1, MUC16, NaPi2b, Nectin-4, PD-1, PD-L1, PSMA, PTK7, SLC44A4, STEAP-1, 5T4 antigen (or TPBG, trophoblast glycoprotein), TF (tissue factor), TF-Ag, Tag72, TNFR, TROP2, VEGFR and VLA.

The linker to be used in accordance with the present invention should comprise a functional group which can react with the thiol group of an uncapped engineered or reduced interchain cysteine, e.g. a maleimide or a haloacetyl group. The linker may be cleavable, e.g. comprising a cleavable dipeptide), or non-cleavable. Suitable cleavable and non-cleavable linkers are known in the art. For instance cleavable linkers may comprise e.g. a valine-citrulline (vc) or a valine-alanine (va) moiety and succinimidyl-4-(N-maleimidomethyl)cyclohexane-1-carboxylate (SMCC) is an example of a non-cleavable linker. Preferably, the linker used is a cleavable linker.

The therapeutic moiety may be a drug, a toxin or a chelator for a radioactive isotope.

Preferred in accordance with the present invention is a process for the preparation of an ADC, wherein the therapeutic moiety is a drug or toxin.

A suitable therapeutic moiety includes a tubulin inhibitor (e.g. a maytansinoid, auristatin or tubulysin derivative), a ribosome-inactivating protein (e.g. a saporin derivative), a DNA minor groove binding agent (e.g. a duocarmycin or pyrrolobenzodiazepine (PBD) dimer or derivative), a DNA damaging agent (e.g. a PBD derivative), a DNA alkylating agent (e.g. a duocarmycin derivative), a DNA intercalating agent (e.g. a calicheamicin derivative), a DNA crosslinking agent (e.g. a 1-(chloromethyl)-2,3-dihydro-1H-benzo[e]indole (CBI) dimer derivative), an RNA polymerase inhibitor (e.g. an amanitin derivative), a DNA cleaving agent (e.g. a calicheamicin derivative) or an agent that disrupts protein synthesis or the function of essential cellular proteins (e.g. a topoisomerase I or II inhibitor (e.g. a camptothecin derivative), a proteasome inhibitor, a histone deacetylase inhibitor, a nuclear export inhibitor, a kinase inhibitor, or an inhibitor of heat shock protein 90).

Preferably, the therapeutic moiety is a duocarmycin, a CBI dimer, a calicheamicin, a PBD, a PBD dimer, a maytansinoid, a tubulysin, a camptothecin, an amanitin, or an auristatin derivative. Most preferably, the therapeutic moiety is a duocarmycin derivative.

Examples of suitable therapeutic moieties include the duocarmycin seco-DUBA, the calicheamicin N-acetyl gamma calicheamicin dimethyl hydrazide (CalichDMH), the PBD dimer SGD-1882, the maytansinoids DM1 and DM4, and the auristatins monomethyl auristatin E (MMAE) and monomethyl auristatin F (MMAF).

Examples of combinations of linker and therapeutic moieties (linker drugs) to be used in the process according to the invention include vc-seco-DUBA (SYD980), mertansine, emtansine, ravtansine, mc-vc-PAB-MMAE (also abbreviated as mc-vc-MMAE or vc-MMAE), mc-MMAF, and mc-vc-MMAF. These abbreviations are well-known to the skilled artisan (see also WO2015/177360). The linker drug vc-seco-DUBA is disclosed in WO2011/133039 as compound 18b on p. 210, ll. 21-27. In a particular embodiment, the process according to the invention, comprises the step (step c.) of conjugating vc-seco-DUBA to the further reduced antibody of step b. as defined hereinabove, in which process preferably the interchain disulfide bond reducing agent in step b. is present in an amount of from 0.5 to 1 molar equivalent per molar equivalent of antibody.

Advantageously, the process according to the invention results in a reaction product, i.e. an ADC, with a negligible amount of unreacted antibody (DAR0). Also the amount of high molecular weight (HMW) species is low in comparison with interchain cysteine-only conjugated ADCs, whereas the average DAR can be easily tuned by varying the amount of interchain disulfide bond reducing agent. The negligible amount of DAR0 facilitates the purification process. Additionally, there is no loss of antibody, which is the most costly part of an ADC. The process according to the invention is thus more efficient than the conjugation processes of the prior art.

The invention also relates to an ADC obtainable by the process described hereinabove.

In one embodiment, the invention relates to an antibody-drug conjugate, wherein the antibody comprises one or more engineered cysteines at positions selected from heavy chain 40, 41, and 89 according to the Kabat numbering system, heavy chain 152, 153, 155, and 171 according to the Eu numbering system, light chain 40 and 41 according to the Kabat numbering system, and light chain 165 and 168 according to the Eu numbering system; wherein therapeutic moieties are conjugated via a cleavable or non-cleavable linker to the one or more engineered cysteines as well as to one or more reduced interchain cysteines of the antibody; and wherein the antibody-drug conjugate has an average DAR of at least 2.0.

Preferably, the invention relates to an ADC as described hereinabove, wherein the antibody comprises one or more engineered cysteines at positions selected from heavy chain 40, 41, 89, 152, and 153; and light chain 40, 41, and 165. More preferably, the invention relates to an ADC as described hereinabove, wherein the antibody comprises one or more engineered cysteines at positions selected from heavy chain 40 and 41, and light chain 40 and 41. Even more preferably, the invention relates to an ADC as described hereinabove, wherein the antibody comprises one or more engineered cysteines at positions selected from heavy chain 41, and light chain 40 and 41. Most preferably, the invention relates to an ADC as described hereinabove, wherein the antibody comprises an engineered cysteine at position HC41.

Preferably, the invention relates to an ADC as described hereinabove wherein the therapeutic moieties conjugated via a cleavable or non-cleavable linker to the one or more engineered cysteines as well as to one or more reduced interchain cysteines of the antibody are selected from the group consisting of tubulin inhibitors (e.g. maytansinoid, auristatin or tubulysin derivatives), ribosome-inactivating proteins (e.g. saporin derivatives), DNA minor groove binding agents (e.g. duocarmycin or pyrrolobenzodiazepine (PBD) dimers or derivatives), DNA damaging agents (e.g. PBD derivatives), DNA alkylating agents (e.g. duocarmycin derivatives), DNA intercalating agents (e.g. calicheamicin derivatives), DNA crosslinking agents (e.g. 1-(chloromethyl)-2,3-dihydro-1H-benzo[e]indole (CBI) dimer derivatives), RNA polymerase inhibitors (e.g. amanitin derivatives), DNA cleaving agents (e.g. calicheamicin derivatives) or agents that disrupt protein synthesis or the function of essential cellular proteins (e.g. topoisomerase I or II inhibitors (e.g. camptothecin derivatives), proteasome inhibitors, histone deacetylase inhibitors, nuclear export inhibitors, kinase inhibitors, or inhibitors of heat shock protein 90).

More preferred is an ADC according to the invention wherein the therapeutic moieties are selected from the group consisting of duocarmycin, CBI dimer, calicheamicin, PBD, PBD dimer, maytansinoid, tubulysin, camptothecin, amanitin, and auristatin derivatives. Most preferably, the therapeutic moieties are selected from the group consisting of duocarmycin derivatives or auristatin derivatives, such as MMAE and MMAF.

Even more preferably, the invention relates to an ADC, wherein the antibody comprises an engineered cysteine at position HC41, and wherein vc-seco-DUBA moieties or vc-MMAE moieties are conjugated to the engineered cysteines and to one or more reduced interchain cysteines and wherein the ADC has an average DAR of at least 2.0.

The optimal average DAR of an ADC is dependent on i.a. the type of tumour associated antigen, the type of antibody, the type of therapeutic moiety, the type of linker and is dependent on the type of cancer. The properties of the antigen, e.g. the level of expression of the tumour associated antigen on the surface of cancer cells, the distribution of the tumour associated antigen in healthy tissue as compared to diseased tissue, and its internalization rate, all influence the optimal DAR of the ADC. Typically, ADCs according to the invention comprising hydrophobic therapeutic moieties will have a lower optimal DAR than ADCs according to the invention comprising less hydrophobic therapeutic moieties, because they form HMW species more easily than ADCs comprising less hydrophobic therapeutic moieties. ADCs comprising less potent therapeutic moieties might require a higher DAR in order to have the desired efficacy.

The skilled person is able to determine the optimal DAR of any ADC for use in the treatment of any type of cancer using conventional analytical techniques, such as SEC and HIC, combined with preclinical in vitro tests (e.g. cytotoxicity against cancer cell lines, using cytolysis or membrane leakage assays) and in vivo experiments (e.g. efficacy in xenograft animal models).

In one preferred embodiment, the ADC according to the invention has an average DAR of at least 2.2. In a second preferred embodiment, the ADC according to the invention has an average DAR of from 2.0 to 6.0, more preferably of from 2.2 to 6.0.

In one embodiment, the invention relates to an ADC, wherein the antibody comprises an engineered cysteine at position heavy chain 41, and wherein vc-seco-DUBA moieties are conjugated to the engineered cysteines and to one or more reduced interchain cysteines and wherein the ADC has an average DAR of from 2.2 to 2.6.

In a second embodiment, the invention relates to an ADC, wherein the antibody comprises an engineered cysteine at position heavy chain 41 and wherein vc-MMAE moieties are conjugated to the engineered cysteines and to one or more reduced interchain cysteines and wherein the ADC has an average DAR of from 2.9 to 5.8.

Advantageously, the ADCs in accordance with the invention are less hydrophobic than analogues with the same DAR which are conjugated via the interchain cysteines only. This reduced hydrophobicity influences the pharmacokinetic properties of the ADC favorably, i.e. less deconjugation and increased efficacy were observed in vivo.

The present invention further relates to a pharmaceutical composition comprising an ADC as described hereinabove and one or more pharmaceutically acceptable excipients. Typical pharmaceutical formulations of therapeutic proteins such as antibodies take the form of lyophilized cakes (lyophilized powders), which require (aqueous) dissolution (i.e. reconstitution) before intravenous infusion, or frozen (aqueous) solutions, which require thawing before use.

Typically, the pharmaceutical composition is provided in the form of a lyophilized cake. Suitable pharmaceutically acceptable excipients for inclusion into the pharmaceutical composition (before freeze-drying) in accordance with the present invention include buffer solutions (e.g. citrate, histidine or succinate containing salts in water), lyoprotectants (e.g. sucrose, trehalose), tonicity modifiers (e.g. sodium chloride), surfactants (e.g. polysorbate), and bulking agents (e.g. mannitol, glycine). Excipients used for freeze-dried protein formulations are selected for their ability to prevent protein denaturation during the freeze-drying process as well as during storage.

The present invention further relates to an ADC or pharmaceutical composition as described hereinabove for use as a medicament, in particular for use in the treatment or prevention of cancer, more particularly for use in the treatment of solid tumours and haematological malignancies.

EXAMPLES

Materials and Methods

An anti-5T4 HC41C antibody comprising a HCVR amino acid sequence of SEQ ID NO:1 as well as a LCVR amino acid sequence of SEQ ID NO:2 was obtained using analogous procedures as the procedures described in WO2015/177360 using HC and LC leader sequences according to SEQ ID NO:3 and 4.

The anti-PSMA cysteine-engineered HC41C antibody was obtained using the materials and procedures described in WO2015/177360. Reagents and buffers were procured from commercial suppliers. Compounds according to formula (I) (i.e. 2-(diphenylphosphino)benzenesulfonic acid) and (II) (i.e. 2-(dicyclohexylphosphino)benzenesulfonic acid), 3-(diphenylphosphino)benzenesulfonic acid, 4-(diphenylphosphino)benzenesulfonic acid, and triphenylphosphine-3,3',3"-trisulfonic acid were purchased from Sigma-Aldrich. The compounds according to formula (III), (IV), (V), (VI) and (VII) were prepared by lithiating benzenesulfonic acid, followed by reacting the lithiated benzenesulfonic acid with the appropriate dialkyl, diaryl or alkyl/aryl (chloro-) phosphine using procedures analogous to literature procedures, e.g. M. Bornand et al., Organometallics, 2007, 26(14), 3585-3596 and T. Schultz et al., Synthesis, 2005, 6, 1005-1011. The linker drug vc-seco-DUBA (SYD980) was synthesized according to procedures as described in WO2011/133039.

Dual Reduction and Conjugation Protocol

To a solution of HC41C engineered antibody (10 mg/ml, 100 mM histidine, pH 5) was added 2-(diphenylphosphino) benzenesulfonic acid (DPPBS, formula (I)) (32 molar equivalents per molar equivalent of the engineered antibody, 10 mM in water (MilliQ®)) and the resulting solution was allowed to stand overnight at room temperature. The selectively reduced antibody solution was rebuffered to 4.2 mM histidine, 50 mM trehalose pH 6 (~10 mg/ml) and treated with EDTA (4% v/v, 25 mM in water (MilliQ®)), TRIS (1% v/v, 1 M in water (MilliQ®), pH 8) and TCEP (0.5-2 molar equivalents (depending on the antibody and the desired DAR) per molar equivalent of the antibody, 3 mM in water (MilliQ®)). The resulting solution was incubated at room temperature for 3.5 hours after which N,N-dimethyl acetamide (DMA) (final DMA concentration 10% v/v) and linker drug (SYD980 or vcMMAE, ~8 molar equivalents per molar equivalent of the antibody, 10 mM in DMA) were added. The resulting mixture was mixed in a roller mixer for 1 hour in the absence of light, subsequently the mixture was allowed to stand at room temperature overnight. Excess linker drug was removed via activated carbon filtration and the resulting clear solution was rebuffered to 4.2 mM histidine, 50 mM trehalose pH 6 using centrifugal filtration. The resulting ADCs were analyzed using HIC/SEC.

Protocol for Conjugation of Linker Drug to Interchain Cysteine Only Using Heavy Chain 41C Engineered Antibody (Using N-Ethylmaleimide Capping of the Engineered Cysteines (Heavy Chain 41C NEM Capped Control))

Wild-type conjugated control HC41C antibodies were synthesized by adding DPPBS (32 molar equivalents per molar equivalent of the antibody, 10 mM in water (MilliQ®)) to a solution of HC41C engineered antibody (10 mg/ml, 100 mM histidine, pH 5). The resulting solution was allowed to stand overnight at room temperature The selectively reduced antibody solution was rebuffered to 4.2 mM histidine, 50 mM trehalose pH 6 (~10 mg/ml) and treated with EDTA (4% v/v, 25 mM in water (MilliQ®)), TRIS (1% v/v, 1 M in water (MilliQ®), pH 8) after which DMA (final DMA concentration was ~10%) and N-ethylmaleimide (NEM, 10 mM in DMA, —3.5 molar equivalents per molar equivalent of the antibody) were added to cap the cysteine at HC41. The resulting solution was incubated at room temperature for 2 hours after the mixture was rebuffered to 4.2 mM histidine, 50 mM trehalose pH 6.

The NEM capped HC41C engineered antibody was treated with EDTA (4% v/v, 25 mM in water (MilliQ®)), TRIS (1% v/v, 1M in water (MilliQ®), pH 8) after which tris(2-carboxyethyl)phosphine (TCEP, 2 mM in water (MilliQ®), 1.33 equivalents) was added. The mixture was incubated at room temperature for 2 hours after which DMA (final DMA concentration was ~10%) and linker drug (SYD980 or vcMMAE) were added (10 mM in DMA, ~7 molar equivalents). After 3 hours activated carbon was added to remove excess linker drug and the solution was filtered and rebuffered to 4.2 mM histidine, 50 mM trehalose pH 6. The resulting ADCs were analyzed using HIC/SEC.

HIC

For analytical HIC, 5-10 μL of sample (1 mg/ml) was injected onto a TSKgel Butyl-NPR column (4.6 mm ID×3.5 cm L, Tosoh Bioscience, Cat. no. 14947). The elution method consisted of a linear gradient from 100% Buffer A (25 mM sodium phosphate, 1.5 M ammonium sulphate, pH 6.95) to 100% of Buffer B (25 mM sodium phosphate, pH 6.95, 20% isopropanol) at 0.4 ml/min over 20 minutes. The column temperature was maintained at 25° C. A Waters Acquity H-Class UPLC system equipped with PDA-detector and Empower software was used. Absorbance was measured at 214 nm to quantify the average DAR and % DAR0.

SEC

Method A

5 µL of sample (1 mg/ml) was injected onto a TSKgel G3000SWXL column (5 µm, 7.8 mm ID×30 cm L, Tosoh Bioscience, Cat. no. 08541) equipped with a TSKgel SWXL Guard column (7 µm, 6.0 mm ID×4.0 cm L, Tosoh Bioscience, Cat. no. 08543). The elution method consisted of elution with 100% 50 mM sodium phosphate, 300 mM NaCl, pH 7.5 at 0.6 ml/min for 30 minutes. The column temperature was maintained at 25° C. A Waters Acquity H-Class UPLC system equipped with PDA-detector and Empower software was used. Absorbance was measured at 214 nm to quantify the amount of HMW species.

Method B 2.5 µL of sample (1 mg/ml) was injected onto an Acquity UPLC Protein BEH SEC column (200 Å, 1.7 µm, 4.6 mm ID×15 cm L, Waters, Cat. no. 186005225). The elution method consisted of elution with a 1:1 mixture of 200 mM sodium phosphate, pH 7.5 and 20% isopropanol in MilliQ® at 0.3 ml/min for 10 minutes. The column temperature was maintained at 40° C. A Waters Acquity H-Class UPLC system equipped with PDA-detector and Empower software was used. Absorbance was measured at 214 nm to quantify the amount of HMW species.

Results

Figure 2:
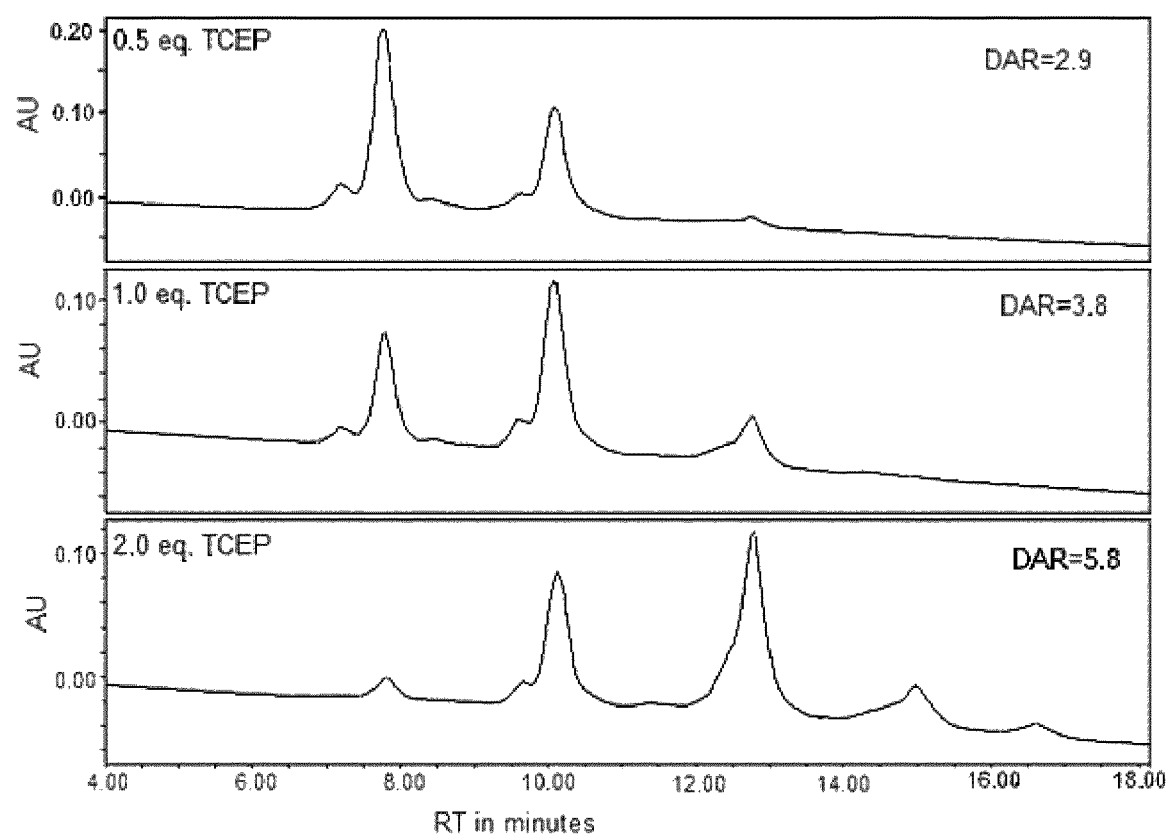
FIG. 2. HIC profiles of vc-MMAE ADCs conjugated via both engineered cysteines at position HC41 and reduced interchain cysteines with increasing DAR, obtained using the process according to the invention with increasing amounts of TCEP.

To various antibodies linker drugs were conjugated using the dual conjugation process. The analytical results are summarized in Table 1. The ADCs conjugated through both the engineered cysteines at HC41 and interchain cysteines contain negligible amounts of DAR0 species and show less HMW species than the ADCs conjugated through interchain cysteines only. Also the retention times of all DAR peaks have decreased, indicative of less hydrophobic DAR species. FIG. 1 shows the difference in HIC profile of an anti-5T4-vc-seco-DUBA ADC conjugated through interchain cysteines only (upper panel) versus an anti-5T4-vc-seco-DUBA ADC conjugated through both the engineered cysteines at HC41 and reduced interchain cysteines (lower panel). The lower panel shows a more homogenous ADC mixture. FIG. 2 shows the HIC profiles of anti-5T4-vc-MMAE ADCs conjugated through both the engineered cysteines at position HC41 and reduced interchain cysteines. The HIC profiles show that the DAR of the ADC can easily be tuned by varying the amount of TCEP in the interchain disulfide bond reduction step.

TABLE 1

| ADC | eq. TCEP | Average DAR | % HMW | % DAR0 | RT DAR4 |
|---|---|---|---|---|---|
| anti-5T4 (HC41C)-vc-seco-DUBA | | | | | |
| 1a | 0 | 1.9 | 1.3$^a$ | 0.4 | NA |
| 1b | 0.25 | 2.2 | 2.6$^a$ | 0.5 | 11.4 |
| 1c | 0.5 | 2.6 | 4.9$^a$ | 0.3 | 11.4 |
| 1d* control | 1.33 | 2.5 | 12.1$^a$ | 22.4 | 12.5 |
| anti-5T4 (HC41C)-vc-MMAE | | | | | |
| 2a | 0.5 | 2.9 | 0.9$^b$ | 0.2 | 10.1 |
| 2b | 1.0 | 3.8 | 0.8$^b$ | 0.1 | 10.1 |
| 2c | 2.0 | 5.8 | 0.6$^b$ | $^c$ | 10.1 |
| 2d* control | 1.16 | 1.7 | 0.6$^b$ | 32.3 | 12.0 |
| anti-PSMA (HC41C)-vc-seco-DUBA | | | | | |
| 3a | 0.25 | 2.0 | 2.7$^b$ | 1.9 | 11.3 |
| 3b | 0.5 | 2.3 | 3.1$^b$ | 2.3 | 11.3 |
| 3c | 0.75 | 2.8 | 3.2$^b$ | 1.5 | 11.3 |
| 3d | 1.0 | 3.2 | 3.2$^b$ | 0.6 | 11.3 |
| 3e control$^d$ | 1.24 | 1.8 | 4.8$^b$ | 38.7 | 12.2 |

NA = not applicable
*HC41C NEM capped control
$^a$SEC Method A
$^b$SEC Method B
$^c$ amount under detection limit
$^d$wt-anti-PSMA -vc-seco-DUBA Apoptosis Assay Experimental LNCaP-C4.2 cells (15,000 cells/well) in complete growth medium (RPMI 1640 media (Lonza; Walkersville, Md., USA) supplemented with 10% v/w FBS, qualified (Gibco-Life Technologies)) were plated in 96-well plates (90 µl/well). After 4 hours of incubation at 37° C., 5% $CO_2$, 10 µl of each anti-PSMA-vc-seco-DUBA ADC (3a, 3b, 3c and 3d) was added. Serial dilutions of each ADC were made in complete growth medium. Apoptosis was assessed after 72 hours using the luminogenic caspase-3/7 substrate from the ApoTox-Glo™ Triplex assay kit of Promega Corporation (Madison, Wis., USA) according to the manufacturer's instructions.

Results

Figure 3:
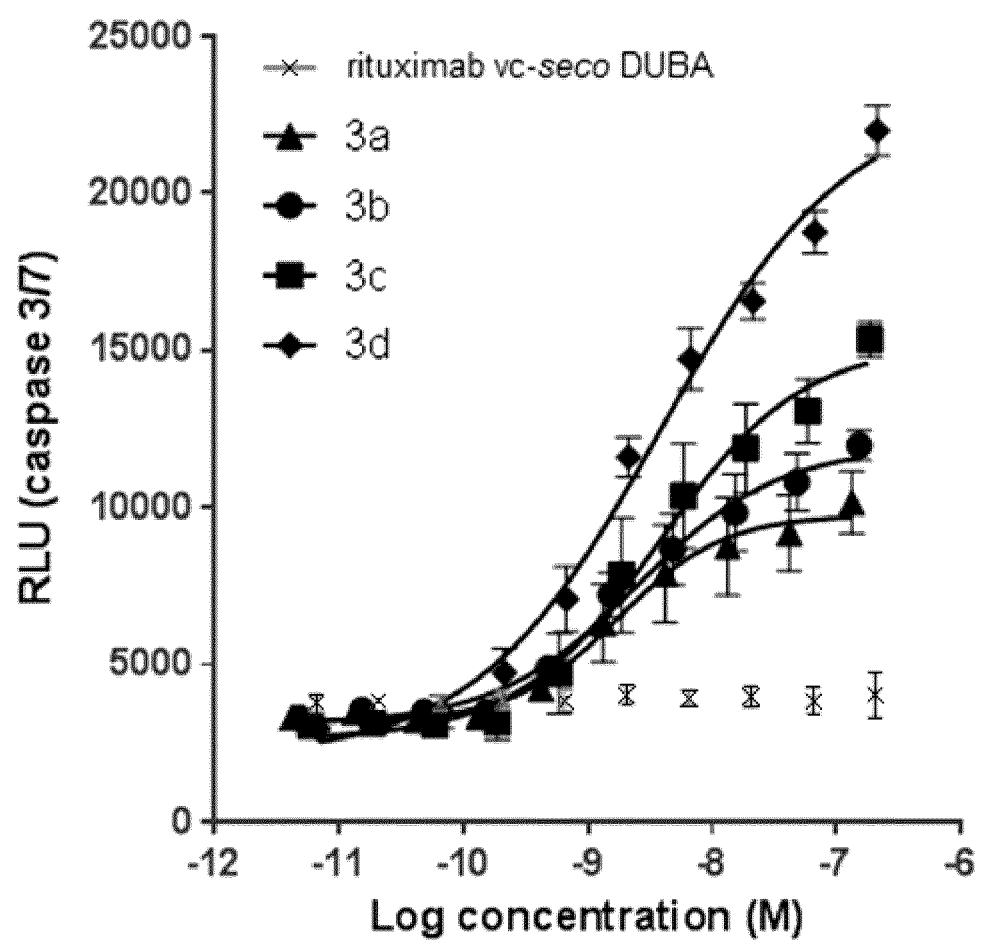
FIG. 3. Caspase 3/7 assay of anti-PSMA-vc-seco-DUBA ADCs 3a-3d conjugated via both engineered cysteines at position HC41 and reduced interchain cysteines with increasing DAR, obtained using the process according to the invention. Rituximab-vc-seco-DUBA is the non-binding ADC control.

FIG. 3 shows that as the DAR of the anti-PSMA-vc-seco-DUBA ADCs increases, the ADCs show increasingly higher caspase-3/7 activity. Higher caspase-3/7 activity is indicative of an increase in apoptosis. Apoptosis is therefore more stimulated by anti-PSMA-vc-seco-DUBA ADCs having a higher DAR as indicated by the higher luminescence signal.

In Vivo Anti-Tumour Efficacy

Tumours were induced through subcutaneous injection of twenty million ($2 \times 10^7$) BT-474 cells in 200 µL RPMI 1640 medium containing matrigel (50:50, v:v, ref: 356237, BD Biosciences, France) into the right flank of female ces1c$^e$ KO nude mice. BT-474 tumour cell implantation was performed 24 to 72 hours after a whole body irradiation with a γ-source (2 Gy, 60Co, BioMep, Dijon, France).

Mice were randomized over the treatment groups when the tumours reached a mean volume of 200-300 mm$^3$ until a group size of 7 animals was achieved. A statistical test (analysis of variance) was performed to assure homogeneity between groups. Next the mice received a single intravenous (tail vein) dose of either vehicle, 1 mg/kg anti-5T4 (HC41C)-vc-seco-DUBA (1b, DAR 2.2), 1 mg/kg anti-5T4 (HC41C)-vc-seco-DUBA (1c, DAR 2.6), 1 mg/kg anti-5T4 (HC41C)-vc-seco-DUBA (1d, interchain cysteine conjugation only, DAR 2.5). Pilot studies have shown that in this model a 1 mg/kg dose of anti-5T4 ADC will not lead to complete tumour remission, allowing the evaluation of the effect of modulations in ADC format. The day of randomization and start of treatment is indicated day 0 (D0).

The length and width of the tumours were measured twice a week with calipers and the volume of the tumours was estimated by the formula: tumour volume=(width$^2 \times$length)/2.

Figure 4:
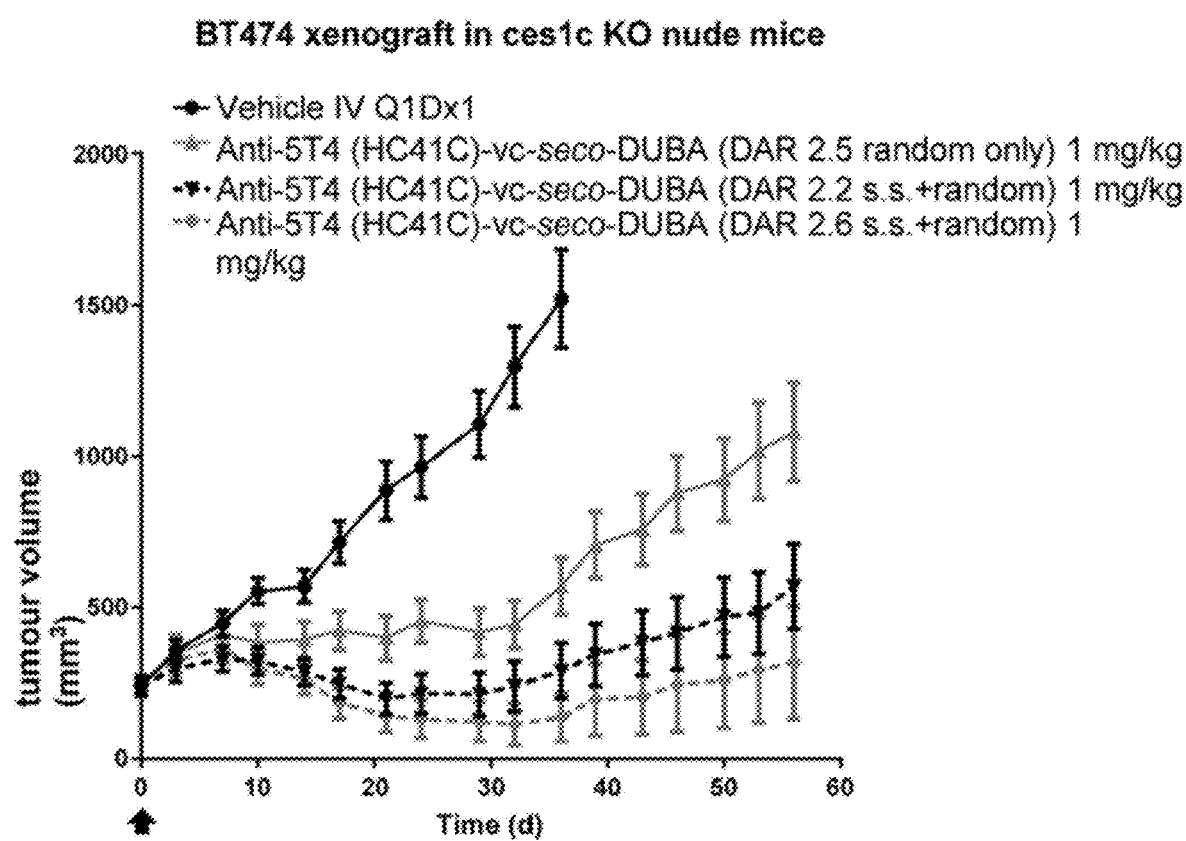
FIG. 4. In vivo efficacy of the anti-5T4-vc-seco-DUBA ADCs 1b (▼, DAR 2.2) and 1c (✱, DAR 2.6) conjugated via both engineered cysteines at position HC41 and reduced interchain cysteines, ADC 1d conjugated via reduced interchain cysteines only (random only, ▲, DAR 2.5) in the BT474 xenograft in $ces1c^e$ KO nude mice.

FIG. 4 shows the in vivo efficacy of the anti-5T4-vc-seco-DUBA ADCs 1b (▼, DAR 2.2) and 1c DAR ( 2.6), both conjugated via both engineered cysteines at position HC41 and reduced interchain cysteines, and ADC 1d, conjugated via reduced interchain cysteines only (random only, ▲, DAR 2.5), in the 5T4-positive BT474 xenograft in ces1c$^e$ KO nude mice. Immediately after dosing all ADCs slowed down tumour growth and after ten days tumour volumes of the anti-5T4-vc-seco-DUBA ADCs 1b and 1c decreased (remission). In contrast, tumours in the mice treated with ADC 1d only slowed down in growth but tumour volumes did not reduce (tumour stasis). After 30 days, tumour regrowth was observed. Clearly, ADCs 1b and 1c showed improved efficacy over ADC 1d.

PK Studies

The treatment groups in this PK study consisted of 9 male and 9 female ces1c$^e$ KO nude mice. The mice received the ADCs 1c or 1d as a single intravenous dose of 3 mg/kg. Blood samples were taken at multiple time point hours after dosing, cooled on ice water, and processed to plasma as soon as possible. Plasma samples were snap frozen in liquid nitrogen and stored at −80° C. until analysis. ADC (Conjugated Ab) levels and total antibody levels (Total Ab) levels in plasma were quantified using an ELISA-based method as described in Dokter et al., Mol. Cancer Ther., 2014, 13, 2618-2629.

Figure 5:
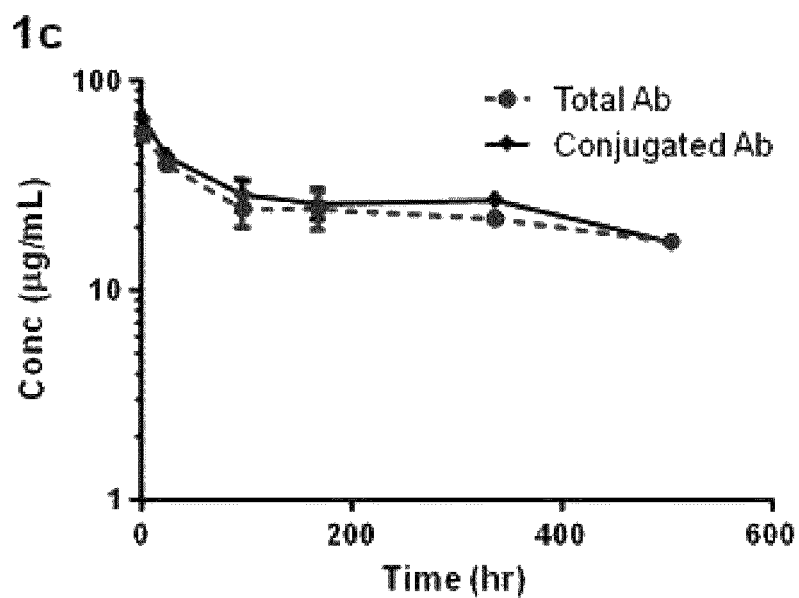
FIG. 5. Full PK curves of the anti-5T4-vc-seco-DUBA ADC 1c (DAR 2.6), conjugated via both engineered cysteines at position HC41 and reduced interchain cysteines, and of the anti-5T4-vc-seco-DUBA ADC 1d (DAR 2.5) that is conjugated via reduced interchain cysteines only.
Figure 5:
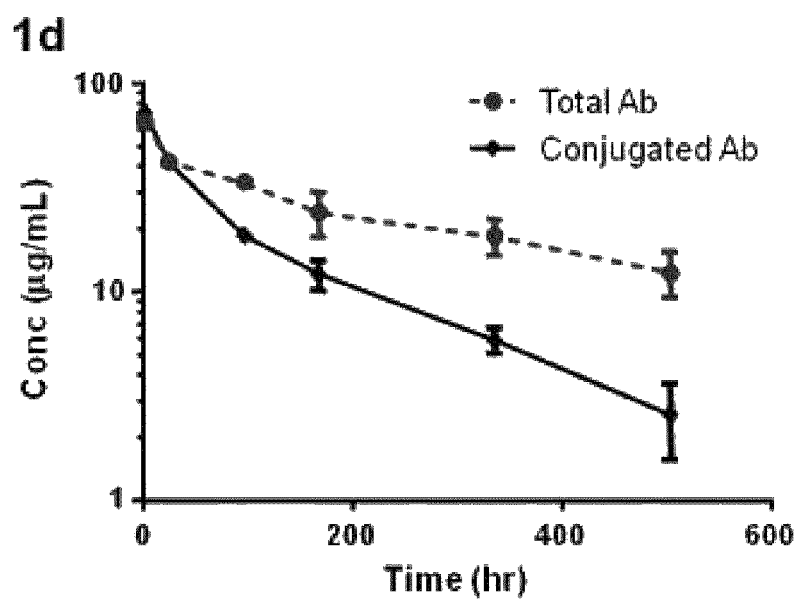

FIG. 5 shows the full PK curves of the ADC 1c (DAR 2.6), conjugated via both engineered cysteines at position HC41 and reduced interchain cysteines, and of the ADC 1d (DAR 2.5) that is conjugated via its reduced interchain cysteines only. For ADC 1c, the levels of Conjugated Ab and Total Ab decrease gradually after 96 hrs, which is indicative of a stable ADC and little deconjugation. However, for ADC 1d the level of Conjugated Ab decreases more steeply than the level of Total Ab. This phenomenon is indicative of deconjugation. ADC 1c is thus less susceptible to deconjugation than ADC 1d.

```
(HCVR anti-5T4 antibody HC41C)
                                                    SEQ ID NO: 1
    1 EVQLVESGGD LAQPGGSLRL SCAVSGIDLS SYGMGWVRQA CGKGLEWVSI

51 ISRNSVTYYA TWAKGRFTIS RDNSKNTVYL QMTSLRAEDT ALYFCARRAT

101 YSGALGYFDI WGQGTLVTVS S (LCVR anti-5T4 antibody)
                                                    SEQ ID NO: 2
    1 EIVMTQSPSS LSASVGDRVT ITCQASENIY STLAWYQQKP GKAPKLLIYD

51 AFDLASGVPS RFSGSGSGTD YTLTISSLQP EDFATYYCQQ GYSGTNVDNA

101 FGQGTKLEIK (HC rabbit leader sequence)
                                                    SEQ ID NO: 3
    1 MGWTLVFLFL LSVTAGVHS (LC rabbit leader sequence)
                                                    SEQ ID NO: 4
    1 MVSSAQFLGL LLLCFQGTRC
```

The invention claimed is:

1. An antibody-drug conjugate comprising an antibody and therapeutic moieties conjugated to cysteine residues in the antibody via a cleavable or non-cleavable linker, wherein said therapeutic moieties are conjugated to one or more engineered cysteines and to one or more reduced interchain cysteines of the antibody, wherein said antibody has an engineered cysteine at heavy chain position 41, or light chain position 40 or 41 according to the Kabat numbering system, or a combination thereof, wherein said antibody-drug conjugate has an average DAR of from 2.0 to 6.0; and wherein said antibody-drug conjugate was made by a process that comprises:

(a) selectively reducing the cysteine-engineered antibody with a compound according to formula (I), (II), (III), (IV), (V), (VI) or (VII)

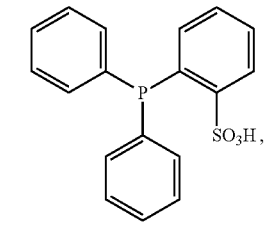

(I)

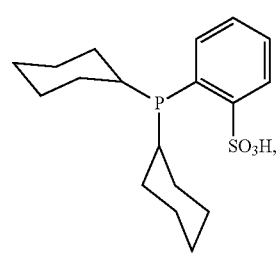

(II)

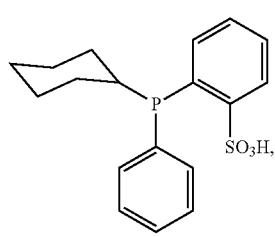

(III)

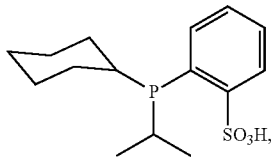

(IV)

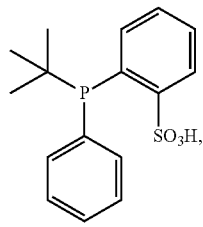

(V)

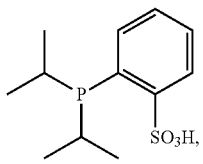

(VI)

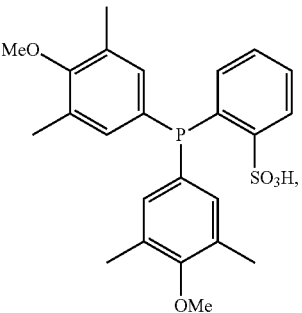

(VII)

or a salt thereof;

(b) further reducing the selectively reduced antibody of step (a) with an interchain disulfide bond reducing agent to form one or more reduced interchain cysteines; and (c) conjugating the therapeutic moieties via cleavable or non-cleavable linkers to the one or more engineered cysteines and to at least one reduced interchain cysteine of the further reduced antibody of step (b) to form said antibody-drug conjugate.

2. An antibody-drug conjugate comprising an antibody and therapeutic moieties conjugated to cysteine residues in said antibody via a cleavable or non-cleavable linker, wherein the antibody comprises one engineered cysteine at heavy chain position 41, light chain position 40 or 41 according to the Kabat numbering system;
  wherein therapeutic moieties are conjugated via the cleavable or non-cleavable linker to the engineered cysteine as well as to one or more reduced interchain cysteines of the antibody; and
  wherein the antibody-drug conjugate has an average DAR of 2.0 to about 3.

3. The antibody-drug conjugate according to claim 2, having an average DAR of 2.2 to about 3.

4. A pharmaceutical composition comprising an antibody-drug conjugate according to claim 2 and one or more pharmaceutically acceptable excipients.

5. The antibody-drug conjugate according to claim 2, wherein the antibody is a monospecific or bispecific antibody or antibody fragment comprising at least one heavy chain and light chain variable region binding to a target selected from the group consisting of annexin A1, B7H4, CA6, CA9, CA15-3, CA19-9, CA27-29, CA125, CA242, CCR2, CCR5, CD2, CD19, CD20, CD22, CD30, CD33, CD37, CD38, CD40, CD44, CD47, CD56, CD70, CD74, CD79, CD115, CD123, CD138, CD203c, CD303, CD333, CEA, CEACAM, CLCA-1, CLL-1, c-MET, Cripto, DLL3, EGFL, EGFR, EPCAM, Eph, endothelin B receptor (ETBR), FAP, FcRL5 (CD307), FGFR, FOLR1, GCC, GPNMB, HER2, HMW-MAA, integrin α, IGF1R, TM4SF1, Lewis A like carbohydrate, Lewis X, Lewis Y, LIV1, mesothelin, MUC1, MUC16, NaPi2b, Nectin-4, PD-1, PD-L1, PSMA, PTK7, SLC44A4, STEAP-1, 5T4 antigen, TF (tissue factor), TF-Ag, Tag72, TNFR, TROP2, VEGFR and VLA.

6. The antibody-drug conjugate according to claim 5, wherein said antibody binds to a target selected from PSMA or 5T4 antigen.

7. The antibody-drug conjugate according to claim 2, wherein said engineered cysteine is at heavy chain position 41.

8. The antibody-drug conjugate according to claim 7, wherein said therapeutic moiety is selected from the group consisting of a duocarmycin, a CBI dimer, a calicheamicin, a PBD, a PBD dimer, a maytansinoid, a tubulysin, a camptothecin, an amanitin, and an auristatin derivative.

9. The antibody-drug conjugate according to claim 8, wherein said therapeutic moiety is a duocarmycin.

10. The antibody-drug conjugate according to claim 8, wherein said linker and therapeutic moiety is vc-seco-DUBA.

11. The antibody-drug conjugate according to claim 10, wherein said average DAR is 2.2 to 2.6.

12. The antibody-drug conjugate according to claim 11, wherein said antibody binds to a target selected from PSMA or 5T4 antigen.

13. The antibody-drug conjugate according to claim 9, wherein the interchain disulfide bond reducing agent is present in an amount of from 0.25 to 2 molar equivalents per molar equivalent of antibody.

14. The antibody-drug conjugate according to claim 13, wherein said disulfide bond reducing agent is tris(3-sulfophenyl)phosphine, tris(2-carboxyethyl)phosphine or dithiothreitol.

15. The antibody-drug conjugate according to claim 14, wherein said antibody has only one engineered cysteine.

16. The antibody-drug conjugate according to claim 15, wherein said average DAR is 2.0 to about 3.

17. The antibody-drug conjugate according to claim 16, wherein said engineered cysteine is at heavy chain position 41.

18. The antibody-drug conjugate according to claim 9, wherein the engineered cysteine antibody is reacted with a compound according to formula (I), (II) or (III), or a salt thereof.

* * * * *